(12) United States Patent
Hastings et al.

(10) Patent No.: US 8,647,281 B2
(45) Date of Patent: Feb. 11, 2014

(54) SYSTEMS AND METHODS FOR MAKING AND USING AN IMAGING CORE OF AN INTRAVASCULAR ULTRASOUND IMAGING SYSTEM

(75) Inventors: Roger N. Hastings, Maple Grove, MN (US); Michael J. Pikus, Golden Valley, MN (US); Kevin D. Edmunds, Ham Lake, MN (US); Tat-Jin Teo, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 580 days.

(21) Appl. No.: 12/415,768

(22) Filed: Mar. 31, 2009

(65) Prior Publication Data

US 2010/0249599 A1 Sep. 30, 2010

(51) Int. Cl.
*A61B 8/00* (2006.01)
*A61B 8/12* (2006.01)

(52) U.S. Cl.
USPC ............ 600/467; 600/459; 600/462; 600/472

(58) Field of Classification Search
USPC ................................................. 600/459, 467
See application file for complete search history.

(56) References Cited

U.S. PATENT DOCUMENTS

| | | | |
|---|---|---|---|
| 4,674,515 A * | 6/1987 | Andou et al. | 600/463 |
| 4,732,156 A | 3/1988 | Nakamura | |
| 4,975,607 A | 12/1990 | Hara | |
| 5,000,185 A | 3/1991 | Yock | |
| 5,095,911 A | 3/1992 | Pomeranz | |
| 5,176,141 A | 1/1993 | Bom et al. | |
| 5,240,003 A * | 8/1993 | Lancee et al. | 600/467 |
| 5,271,402 A | 12/1993 | Yeung et al. | |
| 5,313,950 A | 5/1994 | Ishikawa et al. | |
| 5,314,438 A * | 5/1994 | Shturman | 606/159 |
| 5,353,798 A | 10/1994 | Sieben | |

(Continued)

FOREIGN PATENT DOCUMENTS

DE  3714747  11/1988
DE  10 2004 042927  3/2006

(Continued)

OTHER PUBLICATIONS

Erbel R., et al. "IVUS of micromotors for cardiovascular imaging," Min. Invas. Ther. & Allied Technol. 1997: 6:195-198.

(Continued)

*Primary Examiner* — Tse Chen
*Assistant Examiner* — Patricia Park
(74) *Attorney, Agent, or Firm* — Vidas, Arrett & Steinkraus

(57) ABSTRACT

An imaging assembly for an intravascular ultrasound system includes a catheter, an imaging core, and at least one transducer conductor. The imaging core is insertable into the catheter and extendable from a distal end of the catheter. The imaging core includes a rotatable magnet, a tilted reflective surface, and at least one fixed transducer all disposed in a body. The rotatable magnet is configured and arranged to rotate by a magnetic field generated external to the catheter. The tilted reflective surface rotates with the magnet. The at least one transducer is configured and arranged for transforming applied electrical signals to acoustic signals and also for transforming received echo signals to electrical signals. The at least one transducer conductor is electrically coupled to the at least one transducer and is configured and arranged to extend into the catheter when the imaging core is extended from the catheter.

16 Claims, 7 Drawing Sheets

(56) References Cited

U.S. PATENT DOCUMENTS

| | | |
|---|---|---|
| 5,361,768 A | 11/1994 | Webler et al. |
| 5,373,849 A | 12/1994 | Maroney et al. |
| 5,375,602 A * | 12/1994 | Lancee et al. ................ 600/463 |
| 5,400,788 A | 3/1995 | Dias et al. |
| 5,427,107 A | 6/1995 | Milo et al. |
| 5,443,457 A | 8/1995 | Ginn et al. |
| 5,485,846 A | 1/1996 | Webler et al. |
| 5,503,154 A | 4/1996 | Belef |
| 5,596,989 A | 1/1997 | Morita |
| 5,596,991 A | 1/1997 | Tanaka |
| 5,635,784 A | 6/1997 | Seale |
| 5,715,825 A | 2/1998 | Crowley |
| 5,749,848 A | 5/1998 | Jang et al. |
| 5,771,895 A | 6/1998 | Slager et al. |
| 5,779,643 A * | 7/1998 | Lum et al. .................... 600/462 |
| 5,842,994 A | 12/1998 | TenHoff et al. |
| 5,916,170 A | 6/1999 | Kolz et al. |
| 5,997,523 A | 12/1999 | Jang |
| 6,010,449 A | 1/2000 | Selmon et al. |
| 6,013,033 A | 1/2000 | Berger et al. |
| 6,074,362 A | 6/2000 | Jang et al. |
| 6,078,831 A | 6/2000 | Belef et al. |
| 6,162,179 A | 12/2000 | Moore |
| 6,165,127 A | 12/2000 | Crowley |
| 6,171,234 B1 | 1/2001 | White et al. |
| 6,190,353 B1 | 2/2001 | Makower et al. |
| 6,203,508 B1 | 3/2001 | Ren et al. |
| 6,253,619 B1 | 7/2001 | Danyluk et al. |
| 6,261,246 B1 | 7/2001 | Pantages et al. |
| 6,413,222 B1 | 7/2002 | Pantages et al. |
| 6,459,921 B1 | 10/2002 | Belef et al. |
| 6,482,162 B1 | 11/2002 | Moore |
| 6,529,760 B2 | 3/2003 | Pantages et al. |
| 6,592,520 B1 | 7/2003 | Peszynski et al. |
| 6,658,279 B2 | 12/2003 | Swanson et al. |
| 6,733,457 B2 | 5/2004 | Flesch et al. |
| 6,758,818 B2 | 7/2004 | Pantages et al. |
| 6,796,945 B2 | 9/2004 | Belef et al. |
| 6,814,727 B2 | 11/2004 | Mansouri-Ruiz |
| 6,866,635 B2 | 3/2005 | Flesch et al. |
| 6,945,938 B2 | 9/2005 | Grunwald |
| 6,966,891 B2 | 11/2005 | Ookubo et al. |
| 7,077,808 B2 | 7/2006 | Couvillon, Jr. |
| 7,245,959 B1 | 7/2007 | Wasicek |
| 7,289,842 B2 | 10/2007 | Maschke |
| 7,306,561 B2 | 12/2007 | Sathyanarayana |
| 7,376,455 B2 | 5/2008 | Crowley et al. |
| 7,396,332 B2 | 7/2008 | Taimisto et al. |
| 7,530,953 B2 | 5/2009 | Harshman et al. |
| 7,544,166 B2 * | 6/2009 | Yuan et al. .................... 600/466 |
| 7,666,143 B2 | 2/2010 | Wilser et al. |
| 7,678,056 B2 | 3/2010 | Wilser et al. |
| 2001/0021841 A1 | 9/2001 | Webler et al. |
| 2001/0029337 A1 | 10/2001 | Pantages et al. |
| 2002/0072704 A1 | 6/2002 | Mansouri-Ruiz |
| 2002/0087081 A1 | 7/2002 | Serrano et al. |
| 2002/0151799 A1 | 10/2002 | Pantages et al. |
| 2002/0156515 A1 | 10/2002 | Jang et al. |
| 2002/0188189 A1 | 12/2002 | Belef et al. |
| 2003/0055338 A1 | 3/2003 | Steininger et al. |
| 2003/0097072 A1 | 5/2003 | Serrano et al. |
| 2003/0105509 A1 | 6/2003 | Jang et al. |
| 2003/0114744 A1 | 6/2003 | Pantages et al. |
| 2004/0030220 A1 | 2/2004 | Hamm |
| 2004/0106866 A1 | 6/2004 | Ookubo et al. |
| 2004/0199047 A1 | 10/2004 | Taimisto et al. |
| 2005/0015011 A1 | 1/2005 | Liard et al. |
| 2005/0043618 A1 | 2/2005 | Mansouri-Ruiz |
| 2005/0101859 A1 | 5/2005 | Maschke |
| 2005/0231063 A1 | 10/2005 | Knorre |
| 2005/0288582 A1 | 12/2005 | Yu et al. |
| 2006/0100522 A1 | 5/2006 | Yuan et al. |
| 2006/0173348 A1 | 8/2006 | Wilser et al. |
| 2006/0173350 A1 | 8/2006 | Yuan et al. |
| 2006/0235299 A1 * | 10/2006 | Martinelli .................... 600/434 |
| 2006/0237652 A1 | 10/2006 | Kimchy et al. |
| 2006/0253028 A1 | 11/2006 | Lam et al. |
| 2006/0263890 A1 | 11/2006 | DeCoster |
| 2006/0282153 A1 | 12/2006 | Jang |
| 2007/0016054 A1 | 1/2007 | Cao et al. |
| 2007/0038111 A1 | 2/2007 | Rehrig et al. |
| 2007/0066900 A1 * | 3/2007 | O'Keeffe ...................... 600/459 |
| 2007/0167804 A1 | 7/2007 | Park et al. |
| 2007/0167813 A1 | 7/2007 | Lee et al. |
| 2007/0167821 A1 | 7/2007 | Lee et al. |
| 2007/0167824 A1 | 7/2007 | Lee et al. |
| 2007/0167825 A1 | 7/2007 | Lee et al. |
| 2007/0167826 A1 | 7/2007 | Lee et al. |
| 2007/0178717 A1 | 8/2007 | Harshman et al. |
| 2007/0178767 A1 | 8/2007 | Harshman et al. |
| 2007/0178768 A1 | 8/2007 | Harshman et al. |
| 2007/0232893 A1 | 10/2007 | Tanioka |
| 2007/0239253 A1 | 10/2007 | Jagger et al. |
| 2007/0282197 A1 | 12/2007 | Bill et al. |
| 2008/0009746 A1 * | 1/2008 | Forster et al. ................. 600/467 |
| 2008/0177138 A1 | 7/2008 | Courtney et al. |
| 2008/0200801 A1 | 8/2008 | Wildes et al. |
| 2008/0269615 A1 | 10/2008 | Taimisto et al. |
| 2008/0275304 A1 | 11/2008 | Barbato |
| 2008/0283771 A1 | 11/2008 | Li |
| 2008/0287790 A1 | 11/2008 | Li |
| 2008/0287803 A1 | 11/2008 | Li et al. |
| 2008/0287805 A1 | 11/2008 | Li |
| 2009/0131798 A1 * | 5/2009 | Minar et al. .................. 600/463 |
| 2009/0163818 A1 | 6/2009 | Zelenka et al. |
| 2009/0203991 A1 | 8/2009 | Papaioannou et al. |
| 2009/0264769 A1 | 10/2009 | Sadaka |
| 2009/0275838 A1 | 11/2009 | Marshall et al. |
| 2009/0292204 A1 | 11/2009 | Pansky |
| 2009/0306518 A1 | 12/2009 | Kurse et al. |
| 2010/0036258 A1 | 2/2010 | Dietz et al. |
| 2010/0063398 A1 | 3/2010 | Halmann et al. |
| 2010/0145310 A1 | 6/2010 | Lee et al. |
| 2010/0249599 A1 | 9/2010 | Hastings |
| 2010/0249603 A1 | 9/2010 | Hastings et al. |
| 2010/0249604 A1 | 9/2010 | Hastings et al. |
| 2011/0071400 A1 * | 3/2011 | Hastings et al. .............. 600/467 |
| 2011/0071401 A1 | 3/2011 | Hastings |

FOREIGN PATENT DOCUMENTS

| | | |
|---|---|---|
| EP | 0216998 | 4/1987 |
| EP | 0557127 | 8/1993 |
| EP | 1 143 856 B1 | 7/2004 |
| EP | 1 026 982 B1 | 11/2005 |
| EP | 1 363 540 B1 | 9/2006 |
| EP | 1 707 123 A1 | 10/2006 |
| EP | 1 707 123 B1 | 6/2008 |
| JP | 7000395 | 1/1995 |
| JP | 07/289550 | 11/1995 |
| JP | 09/047455 | 2/1997 |
| WO | 92/03095 | 3/1992 |
| WO | 92/16147 | 10/1992 |
| WO | 94/00052 | 1/1994 |
| WO | 94/16625 | 8/1994 |
| WO | 95/32539 | 11/1995 |
| WO | WO-96/11634 | 4/1996 |
| WO | WO-97/17898 | 5/1997 |
| WO | WO-97/28743 | 8/1997 |
| WO | 99/08596 | 2/1999 |
| WO | 99/08597 | 2/1999 |
| WO | WO-99/16347 | 4/1999 |
| WO | 99/40853 | 8/1999 |
| WO | WO-00/07500 | 2/2000 |
| WO | WO-00/18463 | 4/2000 |
| WO | WO-00/33741 | 6/2000 |
| WO | WO-01/68173 A2 | 9/2001 |
| WO | WO-01/78821 A1 | 10/2001 |
| WO | WO-02/053034 A2 | 7/2002 |
| WO | WO-02/069806 A2 | 9/2002 |
| WO | WO-03/103501 A1 | 12/2003 |
| WO | WO-03/103502 A1 | 12/2003 |
| WO | WO-2004/014233 A1 | 2/2004 |
| WO | 2004/042546 | 5/2004 |

(56) References Cited

FOREIGN PATENT DOCUMENTS

| | | |
|---|---|---|
| WO | 2006000259 | 1/2006 |
| WO | 2006/113857 | 10/2006 |
| WO | 2007/025230 | 3/2007 |
| WO | WO-2007/090066 A2 | 8/2007 |
| WO | 2009/094341 | 7/2009 |
| WO | 2009/129438 | 10/2009 |
| WO | 2009/137403 | 11/2009 |
| WO | 2009/141690 | 11/2009 |
| WO | 2009137659 | 11/2009 |
| WO | 2009/149315 | 12/2009 |

OTHER PUBLICATIONS

International Search Report and Written Opinion for International Application No. PCT/US2010/049392, mailed on Dec. 7, 2010.

Esashi M et al.; "Biomedical Microsystems for Minimally Invasive Diagnosis and Treatment", Proceedings of the IEEE. Vol. 92. No. 1, Jan. 2004; pp. 98-114.

Jun Keun Chang et al.; "Development of endovascular microtools", Journal of Micromechanics & Microengineering, Institute of Physics Publishing, vol. 12, No. 6, Nov. 2002, pp. 824-831.

Lancee, C.T. et al.; Future Directions in Intravascular Ultrasound: From Micro-Motors to Imaging Guidewire Systems; Echocardiography: A Jml. of CV Ultrasound & Allied Tech.; vol. 12, No. 3, 1995; pp. 275-281.

Long-Sheng Fan et al.; IC-Processed Electrostatic Micro-motors; 19881211; 19881211-19881214; Dec. 11, 1988, pp. 666-669.

International Search Report and Written Opinion for International Application No. PCT/US2010/028439, mailed on Sep. 6, 2010.

International Search Report and Written Opinion for International Application No. PCT/US2010/028440, mailed on Nov. 19, 2010.

International Search Report and Written Opinion for International Application No. PCT/US2010/028454, mailed on Jun. 8, 2011.

International Search Report and Written Opinion for International Application No. PCT/US2010/049384, mailed Mar. 21, 2011.

* cited by examiner

SYSTEMS AND METHODS FOR MAKING AND USING AN IMAGING CORE OF AN INTRAVASCULAR ULTRASOUND IMAGING SYSTEM

TECHNICAL FIELD

The present invention is directed to the area of intravascular ultrasound imaging systems and methods of making and using the systems. The present invention is also directed to intravascular ultrasound systems having an imaging core that includes a rotatable magnet driven by magnetic field windings external to the patient, as well as methods of making and using the imaging cores and intravascular ultrasound systems.

BACKGROUND

Intravascular ultrasound ("IVUS") imaging systems have proven diagnostic capabilities for a variety of diseases and disorders. For example, IVUS imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety is diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor.

BRIEF SUMMARY

In one embodiments, an imaging assembly for an intravascular ultrasound system includes a catheter, an imaging core, and at least one transducer conductor. The catheter has a longitudinal length, a distal end, and a proximal end. The catheter defines a lumen extending along the longitudinal length of the catheter from the proximal end to the distal end and is configured and arranged for insertion into the vasculature of a patient. The imaging core has a longitudinal length that is substantially less than the longitudinal length of the catheter and is configured and arranged for being disposed in the lumen and also for extending out from the distal end of the catheter. The imaging core includes a body, a rotatable magnet, a tilted reflective surface, and at least one fixed transducer. The body has a proximal end and a distal end and defines at least one inner chamber. The rotatable magnet is disposed in the body and is configured and arranged to be driven to rotate by a magnetic field generated external to the catheter. The tilted reflective surface is configured and arranged to rotate with the magnet. The at least one fixed transducer is disposed in the body and is configured and arranged for transforming applied electrical signals to acoustic signals and also for transforming received echo signals to electrical signals. The at least one transducer conductor is electrically coupled to the at least one transducer and is configured and arranged to extend out from the body and into the lumen of the catheter when the imaging core is extended from the catheter.

In another embodiment, an imaging assembly for an intravascular ultrasound system includes a guidewire, an imaging core configured and arranged for coupling to the guidewire, and at least one transducer conductor coupled to the imaging core. The guidewire is configured and arranged for insertion into the vasculature of a patient. The imaging core includes a rotary unit and at least one fixed transducer disposed in a body. The body has a proximal end, a distal end, and defines a lumen extending along a longitudinal length of the body. The lumen is configured and arranged to receive the guidewire. The rotary unit is disposed in the body and rotatable in response to a magnetic field generated external to the imaging assembly. The rotary unit includes a rotatable magnet, a tilted reflective surface, and a sonolucent material all configured and arranged to rotate at the same rotational velocity. The tilted reflective surface is disposed at one end of a longitudinal length of the magnet and a sonolucent material is disposed over the reflective tilted surface. The at least one fixed transducer is positioned at the proximal end of the body and is configured and arranged for transforming applied electrical signals to acoustic signals and also for transforming received echo signals to electrical signals. The at least one transducer conductor is electrically coupled to the at least one transducer and is in electrical communication with a pulse generator configured and arranged for providing electric signals to the at least one transducer.

In yet another embodiment, an imaging assembly for an intravascular ultrasound system includes a catheter, an imaging core, and at least one transducer conductor. The catheter has a longitudinal length, a distal end, and a proximal end. The catheter defines a lumen extending along the longitudinal length of the catheter from the proximal end to the distal end and is configured and arranged for insertion into the vasculature of a patient. The imaging core has a longitudinal length that is substantially less than the longitudinal length of the catheter and is configured and arranged for being disposed in a distal end of the lumen. The imaging core includes at least one transducer, a transformer, and a magnet. The at least one transducer is configured and arranged for transforming applied electrical signals to acoustic signals and also for transforming received echo signals to electrical signals. The transformer includes a rotating component and a stationary component spaced apart from one another. The rotating component is coupled to the at least one transducer and is configured and arranged to rotate the at least one transducer. The magnet is configured and arranged to be driven to rotate by a magnetic field generated external to the catheter. The magnet is coupled to, or disposed on, at least one of the rotating component of the transformer or the at least one transducer. The at least one transducer conductor is electrically coupled to the stationary component of the transformer and extends to the proximal end of the catheter.

In another embodiment, a method for imaging a patient using an intravascular ultrasound imaging system includes inserting a catheter into patient vasculature. The catheter includes an imaging core disposed in a lumen defined in the catheter. The imaging core is electrically coupled to a control module by at least one transducer conductor. The imaging core has a longitudinal axis and includes at least one fixed transducer and a magnet that rotates by application of a magnetic field generated external to the catheter. The transducer emits acoustic signals directed at a tilted reflected surface configured and arranged to rotate with the magnet. The imaging core is extended out from a distal end of the catheter so that the imaging core remains coupled to the control module via the at least one transducer conductor. At least one electrical signal is transmitted from the control module to the at least one transducer. A magnetic field is generated to cause the magnet to rotate. At least one acoustic signal is transmitted from the at least one transducer to patient tissue via reflection from the reflective surface of the magnet. At least one echo signal is received from a tissue-boundary between adjacent imaged patient tissue by the imaging core. At least one transformed echo signal is transmitted from the at least one transducer to the control module for processing.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of intravascular ultrasound imaging systems and methods of making and using the systems. The present invention is also directed to intravascular ultrasound systems having an imaging core that includes a rotatable magnet driven by magnetic field windings external to the patient, as well as methods of making and using the imaging cores and intravascular ultrasound systems.

Suitable intravascular ultrasound ("IVUS") imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,306,561; and 6,945,938; as well as U.S. Patent Application Publication Nos. 20060253028; 20070016054; 20070038111; 20060173350; and 20060100522, all of which are incorporated by reference.

Figure 1:
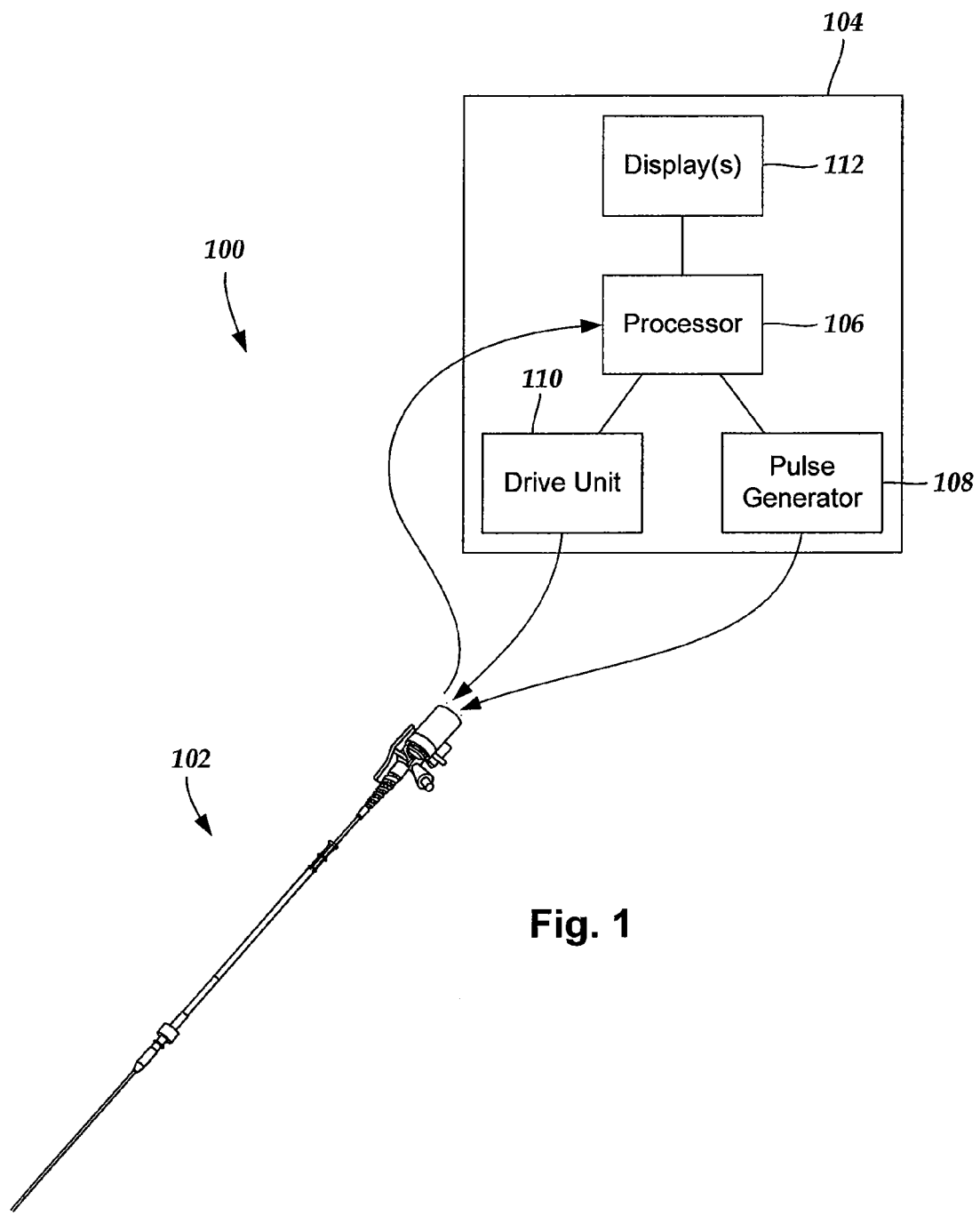
FIG. 1 is a schematic view of one embodiment of an intravascular ultrasound imaging system, according to the invention.

FIG. 1 illustrates schematically one embodiment of an IVUS imaging system 100. The IVUS imaging system 100 includes a catheter 102 that is coupleable to a control module 104. The control module 104 may include, for example, a processor 106, a pulse generator 108, a motor 110, and one or more displays 112. In at least some embodiments, the pulse generator 108 forms electric pulses that may be input to one or more transducers (312 in FIG. 3) disposed in the catheter 102. In at least some embodiments, mechanical energy from the motor 110 may be used to drive an imaging core (306 in FIG. 3) disposed in the catheter 102. In at least some embodiments, electric pulses transmitted from the one or more transducers (312 in FIG. 3) may be input to the processor 106 for processing. In at least some embodiments, the processed electric pulses from the one or more transducers (312 in FIG. 3) may be displayed as one or more images on the one or more displays 112. In at least some embodiments, the processor 106 may also be used to control the functioning of one or more of the other components of the control module 104. For example, the processor 106 may be used to control at least one of the frequency or duration of the electrical pulses transmitted from the pulse generator 108, the rotation rate of the imaging core (306 in FIG. 3) by the motor 110, the velocity or length of the pullback of the imaging core (306 in FIG. 3) by the motor 110, or one or more properties of one or more images formed on the one or more displays 112.

Figure 2:
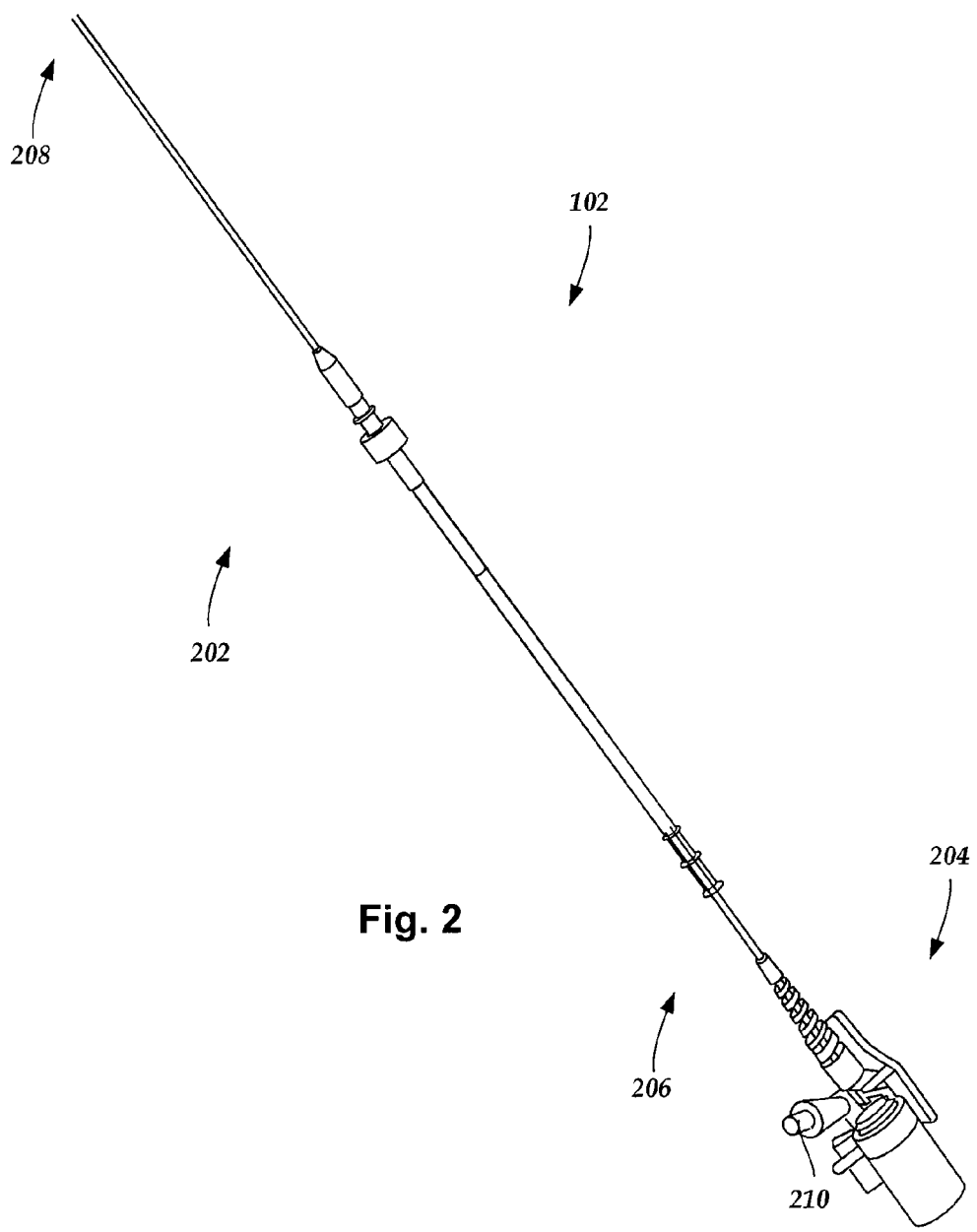
FIG. 2 is a schematic side view of one embodiment of a catheter of an intravascular ultrasound imaging system, according to the invention.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. In at least some embodiments, the catheter 102 defines at least one flush port, such as flush port 210. In at least some embodiments, the flush port 210 is defined in the hub 204. In at least some embodiments, the hub 204 is configured and arranged to couple to the control module (104 in FIG. 1). In some embodiments, the elongated member 202 and the hub 204 are formed as a unitary body. In other embodiments, the elongated member 202 and the catheter hub 204 are formed separately and subsequently assembled together.

Figure 3:
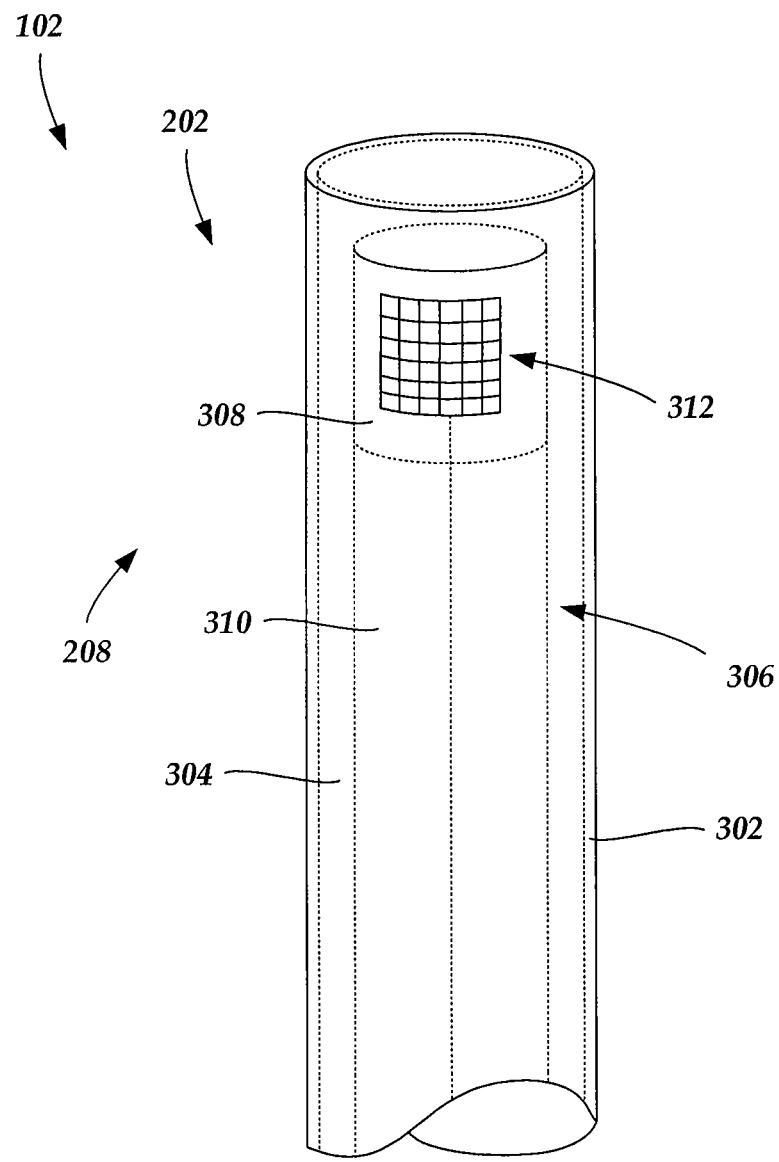
FIG. 3 is a schematic perspective view of one embodiment of a distal end of the catheter shown in FIG. 2 with an imaging core disposed in a lumen defined in the catheter, according to the invention.

FIG. 3 is a schematic perspective view of one embodiment of the distal end 208 of the elongated member 202 of the catheter 102. The elongated member 202 includes a sheath 302 and a lumen 304. An imaging core 306 is disposed in the lumen 304. The imaging core 306 includes an imaging device 308 coupled to a distal end of a rotatable driveshaft 310.

The sheath 302 may be, formed from any flexible, biocompatible material suitable for insertion into a patient. Examples of suitable materials include, for example, polyethylene, polyurethane, plastic, spiral-cut stainless steel, nitinol hypotube, and the like or combinations thereof.

One or more transducers 312 may be mounted to the imaging device 308 and employed to transmit and receive acoustic pulses. In a preferred embodiment (as shown in FIG. 3), an array of transducers 312 are mounted to the imaging device 308. In other embodiments, a single transducer may be employed. In yet other embodiments, multiple transducers in an irregular-array may be employed. Any number of transducers 312 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used.

The one or more transducers 312 may be formed from one or more known materials capable of transforming applied electrical pulses to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like.

The pressure distortions on the surface of the one or more transducers 312 form acoustic pulses of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic pulses of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a conductive acoustic lens and a conductive backing material formed from an acoustically absorbent material (e.g., an epoxy substrate with tungsten particles). During operation, the piezoelectric layer may be electrically excited by both the backing material and the acoustic lens to cause the emission of acoustic pulses.

In at least some embodiments, the one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

In at least some embodiments, the imaging core 306 may be rotated about a longitudinal axis of the catheter 102. As the imaging core 306 rotates, the one or more transducers 312 emit acoustic pulses in different radial directions. When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic pulses transmitted and the echo pulses received. In at least some embodiments, the rotation of the imaging core 306 is driven by the motor 110 disposed in the control module (104 in FIG. 1).

As the one or more transducers 312 rotate about the longitudinal axis of the catheter 102 emitting acoustic pulses, a plurality of images are formed that collectively form a radial cross-sectional image of a portion of the region surrounding the one or more transducers 312, such as the walls of a blood vessel of interest and the tissue surrounding the blood vessel. In at least some embodiments, the radial cross-sectional image can be displayed on one or more displays 112.

In at least some embodiments, the imaging core 306 may also move longitudinally along the blood vessel within which the catheter 102 is inserted so that a plurality of cross-sectional images may be formed along a longitudinal length of the blood vessel. In at least some embodiments, during an imaging procedure the one or more transducers 312 may be retracted (i.e., pulled back) along the longitudinal length of the catheter 102. In at least some embodiments, the catheter 102 includes at least one telescoping section that can be retracted during pullback of the one or more transducers 312. In at least some embodiments, the motor 110 drives the pullback of the imaging core 306 within the catheter 102. In at least some embodiments, the motor 110 pullback distance of the imaging core is at least 5 cm. In at least some embodiments, the motor 110 pullback distance of the imaging core is at least 10 cm. In at least some embodiments, the motor 110 pullback distance of the imaging core is at least 15 cm. In at least some embodiments, the motor 110 pullback distance of the imaging core is at least 20 cm. In at least some embodiments, the motor 110 pullback distance of the imaging core is at least 25 cm.

The quality of an image produced at different depths from the one or more transducers 312 may be affected by one or more factors including, for example, bandwidth, transducer focus, beam pattern, as well as the frequency of the acoustic pulse. The frequency of the acoustic pulse output from the one or more transducers 312 may also affect the penetration depth of the acoustic pulse output from the one or more transducers 312. In general, as the frequency of an acoustic pulse is lowered, the depth of the penetration of the acoustic pulse within patient tissue increases. In at least some embodiments, the IVUS imaging system 100 operates within a frequency range of 5 MHz to 60 MHz.

In at least some embodiments, one or more conductors 314 electrically couple the transducers 312 to the control module 104 (See FIG. 1). In at least some embodiments, the one or more conductors 314 extend along a longitudinal length of the rotatable driveshaft 310.

In at least some embodiments, the catheter 102 with one or more transducers 312 mounted to the distal end 208 of the imaging core 308 may be inserted percutaneously into a patient via an accessible blood vessel, such as the femoral artery, at a site remote from the selected portion of the selected region, such as a blood vessel, to be imaged. The catheter 102 may then be advanced through the blood vessels of the patient to the selected imaging site, such as a portion of a selected blood vessel.

It is desirable to have uniform rotation of the imaging core 306 during operation. When the catheter 102 is advanced through blood vessels of the patient, the catheter 102 may navigate one or more tortuous regions or one or more narrow regions which may press against one or more portions of the catheter 102 and cause a non-uniform rotation (e.g., a wobble, a vibration, or the like) of the imaging core 306 during operation. Non-uniform rotation may lead to the distortion of a subsequently-generated IVUS image. For example, non-uniform rotation of the imaging core 306 may cause the subsequently-generated IVUS image to be blurred.

In conventional systems, a rotational motor is disposed in a proximal portion of the catheter 302 or in a unit to which the proximal portion of the catheter is attached. Due to the distance between a proximally-positioned rotational motor and an imaging core and the tortuous nature of the vasculature into which the distal end of the catheter is positioned during operation, non-uniform rotation can be difficult to prevent.

A motor capable of rotating the imaging core is described. The motor includes a rotatable magnet disposed in the imaging core driven by a plurality of magnetic field windings external to the imaging core. In at least some embodiments, the described motor reduces, or even eliminates non-uniform rotation caused by one or more off-axis forces (e.g., blood vessel walls pressing against portions of the imaging core). In at least some embodiments, the imaging core is configured and arranged for extending outward from a catheter. In at least some embodiments, the imaging core is configured and arranged for coupling to a guidewire. In at least some embodiments, the imaging core has an outer diameter small enough to allow imaging procedures to be performed from target imaging sites in the brain of a patient, such as one or more of the cerebral arteries.

The magnetic field windings ("windings") include one or more turns of an elongated conductor (e.g., a wire, or the like) that form a rotating magnetic field. The rotating magnetic field produces a torque on the magnet. The torque causes the magnet to rotate. The windings may be provided power from any suitable power source (e.g., the control module, or other power source).

In at least some embodiments, the windings are disposed external to a patient into which the magnet is disposed (i.e., the windings are extracorporeal). It may be an advantage to position the windings external to the patient. Externally positioned windings eliminate the need for the windings to be wrapped over an outer surface of the magnet. Thus, the diameter of the imaging core, which is insertable into the patient, may be reduced. Therefore, imaging systems using extracorporeal windings may be insertable into patient vasculature that was previously too small to be imaged with conventional systems. Additionally, extracorporeal windings may also have the advantage of eliminating the need for disposing motor conductors within the patient for providing power to operate the motor. Moreover, another potential advantage to extracorporeal windings is that the windings may be formed from lower-cost materials than internal windings because the windings do not need to be miniaturized or fabricated from materials suitable for insertion into a patient. Extracorporeal windings also may not need to be cooled or use superconductors to generate a large enough magnetic field to drive rotation of the magnet. Additionally, when an imaging system uses windings that are cooled or uses superconductors (e.g., to generate a larger magnetic field, or the like), it is typically easier to cool the windings or use superconductors when the windings are disposed external to a patient than when the windings are disposed in a patient.

In at least some embodiments, an imaging core can be delivered to a target imaging site using a catheter (102 in FIG. 1). In at least some embodiments, the imaging core can disposed in a distal end of the catheter. In at least some embodiments, the imaging core can be extended outside of the catheter. In at least some embodiments, the imaging core can be extended outwardly from the distal end of the catheter. It will be understood that the imaging core can also be operated either while disposed in the catheter or extended outside of the catheter. In at least some embodiments, the imaging core can extend from the catheter at least 6 cm. In at least some embodiments, the imaging core can extend from the catheter at least 8 cm. In at least some embodiments, the imaging core can extend from the catheter at least 10 cm. In at least some embodiments, the imaging core can extend from the catheter at least 12 cm.

In at least some embodiments, when the imaging core is extended from the distal end of the catheter, movement of the imaging core is directed by blood flow within the vasculature in which the imaging core is positioned. In at least some embodiments, when the imaging core is extended from the distal end of the catheter, the imaging core remains tethered to at least one of the catheter or to the control module (104 in FIG. 1) via the catheter. In at least some embodiments, the imaging core remains tethered to at least one of the catheter or to the control module via one or more transducer conductors configured and arranged to allow the imaging core to orient in axes that are not the same as the distal end of the catheter. In at least some embodiments, the one or more transducer conductors are floppy. In at least some embodiments, the imaging core can be maintained in a position that is tilted relative to the catheter or the blood vessel in which the imaging core is disposed. In at least some embodiments, one or more additional elongated connectors (e.g., push and pull wires, or the like) may be used to maintain the tilted position.

In at least some embodiments, the imaging core is maintained in a position that is tilted relative to the catheter or the blood vessel in which the imaging core is disposed by the orientation of the applied magnetic field vector. For example, as discussed below, a rotating magnetic field is generally in a plane perpendicular to the imaging core. When, however, the plane of the rotating magnetic field vector is tilted relative to this plane, the imaging core will tilt to align its magnetic field vector with the applied magnetic field vector.

Figure 4:
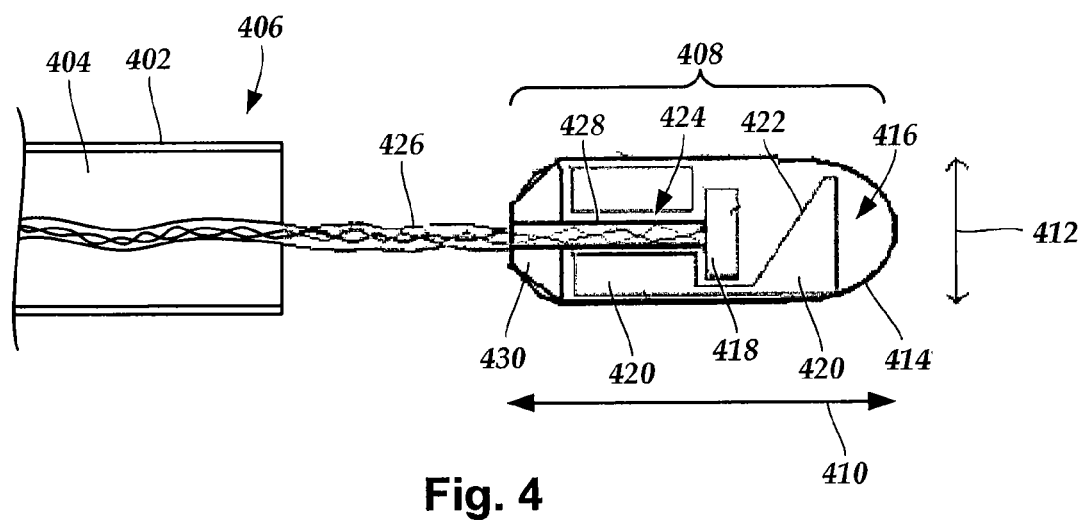
FIG. 4 is a schematic longitudinal cross-sectional view of one embodiment of an imaging core coupled to one or more transducer conductors extending from a lumen of a catheter, according to the invention.

FIG. 4 is a schematic longitudinal cross-sectional view of one embodiment of a catheter 402 defining a lumen 404 at a distal end 406 of the catheter 402. An imaging core 408 extends from the lumen 404 of the catheter 402. The imaging core 408 has a longitudinal length 410 and a diameter 412.

The imaging core 408 includes a body 414 that defines an inner chamber 416. One or more fixed transducers 418 and a rotatable magnet 420 are disposed in the body 414. In at least some embodiments, the magnet 420 has a longitudinal axis that is parallel to the longitudinal length 410 of the imaging core 408. In at least some embodiments, the magnet 420 rotates about the longitudinal axis and includes a tilted reflective surface 422. The reflective surface 422 may be a reflective surface 422 of the magnet 420 or a reflective surface 422 either disposed on the magnet 420 or coupled to the magnet 420.

In at least some embodiments, the magnet 420 is disposed proximal to the one or more transducers 418. In at least some embodiments, at least a portion of the magnet 420 is disposed distal to the one or more transducers 418. In at least some embodiments, at least a portion of the magnet 420 is disposed proximal to the one or more transducers 418 and at least a portion of the magnet 420 is disposed distal to the one or more transducers 418.

The reflective surface 422 is tilted at an angle that is not parallel with either the longitudinal length 410 or the diameter 412 of the imaging core 408. The magnet 420 defines an aperture 424 extending along at least a portion of the magnet 420. One or more transducer conductors 426 are electrically coupled to the one or more fixed transducers 418 and extend from the body 414 into the lumen 404 of the catheter 402. In at least some embodiments, the one or more transducer conductors 426 are in electrical communication with the control module (104 in FIG. 1).

In at least some embodiments, the body 414 of the imaging core 408 includes a fixed shaft 428 coupling the one or more fixed transducers 418 to a proximal end of the body 414. In at least some embodiments, at least a portion of the one or more transducer conductors 426 extends within the fixed shaft 428. In at least some embodiments, the fixed shaft 428 extends within the aperture 424 of the magnet 420. In at least some embodiments, the imaging core 408 includes at least one support hub 430. In at least some embodiments, the at least one support hub 430 is positioned at a proximal end of the imaging core 408. In at least some embodiments, the fixed shaft 428 extends through the at least one support hub 430. In at least some embodiments, the at least one support hub 430 is configured and arranged for providing support to the imaging core 408 to increase the amount of off-axis forces (e.g., blood vessel walls pressing against portions of the imaging core) needed to cause non-uniform rotation of the magnet 420.

In at least some embodiments, the diameter 412 of the imaging core 408 is no greater than 1.1 millimeters. In at least some embodiments, the diameter 412 of the imaging core 408 is no greater than 1.0 millimeter. In at least some embodiments, the diameter 412 of the imaging core 408 is no greater than 0.9 millimeters. In at least some embodiment, the longitudinal length 410 of the imaging core 408 is substantially less than a longitudinal length of the catheter 402.

The body 414 can be formed from any biocompatible, sonolucent material. In at least some embodiments, the body 414 is formed from a material that is fluidtight. In at least some embodiments, the inner chamber 416 is filled with one or more sonolucent fluids. In at least some embodiments, the one or more sonolucent fluids have impedance that matches patient fluids or tissues in proximity to target imaging sites. In at least some embodiments, the inner chamber 416 is filled with a magnetic fluid suspension ("ferrofluid") (e.g., a suspension of magnetic nano-particles, such as available from the Ferrotec Corp., Santa Clara, Calif.). The ferrofluid is attracted to the magnet 420 and remains positioned at an outer surface of the magnet 420 as the magnet 420 rotates. The fluid shears near the walls of non-rotating surfaces (e.g., inner surfaces of the body 414), such that the rotating magnet 420 does not physically contact these non-rotating surfaces. The resulting viscous drag torque on the magnet 420 increases in proportion to the rotation frequency of the magnet 420, and may be reduced relative to a non-lubricated design.

In at least some embodiments, the imaging core 408 is configured and arranged for being disposed in the lumen 404 during insertion of the catheter 402 into a patient and extended from the distal end 406 of the catheter 402 in proximity to a target imaging site. In at least some embodiments, the body 414 has a shape conducive to maintaining the imaging core 408 in proximity to a transverse center of a blood vessel when the imaging core 408 is extended from the catheter 402 in a blood vessel with flowing blood. In at least some embodiments, an exterior surface of the body 414 includes one or more fins to direct movement of the imaging core 408 within a blood vessel.

The one or more transducers 418 are configured and arranged to output and receive acoustic signals. In at least some embodiments, the acoustic signals are transmitted in a direction parallel to the longitudinal length 410 of the imaging core 408. In at least some embodiments, the reflective surface 422 is tilted at an angle so that acoustic signals output from one or more transducers 418 are reflected to a direction that is not parallel to the longitudinal length 410 of the imaging core 408. In at least some embodiments, the reflective surface 422 is tilted at an angle so that acoustic signals output from one or more fixed transducers 418 are reflected to a direction that is roughly perpendicular to the longitudinal length 410 of the imaging core 408.

The reflective surface 422 is tilted at an angle so that at least some of the echo signals from patient tissue interfaces are reflected to the one or more transducers 418. In at least some embodiments, the reflective surface 422 is tilted at an angle so that at least some of the echo signals from patient tissue interfaces are reflected to a direction that is parallel to the longitudinal length 410 of the imaging core 408.

In at least some embodiments, one or more sonolucent materials are disposed over the reflective surface 422. In at least some embodiments, the one or more sonolucent materials have impedance that matches patient fluids or tissues in proximity to target imaging sites. In at least some embodiments, the one or more sonolucent materials are configured and arranged so that the magnet 420 and sonolucent material(s) have an even weight distribution around the axis of rotation of the magnet 420. In at least some embodiments, the magnet 420 and the sonolucent material(s) collectively are substantially cylindrically shaped.

Figure 5:
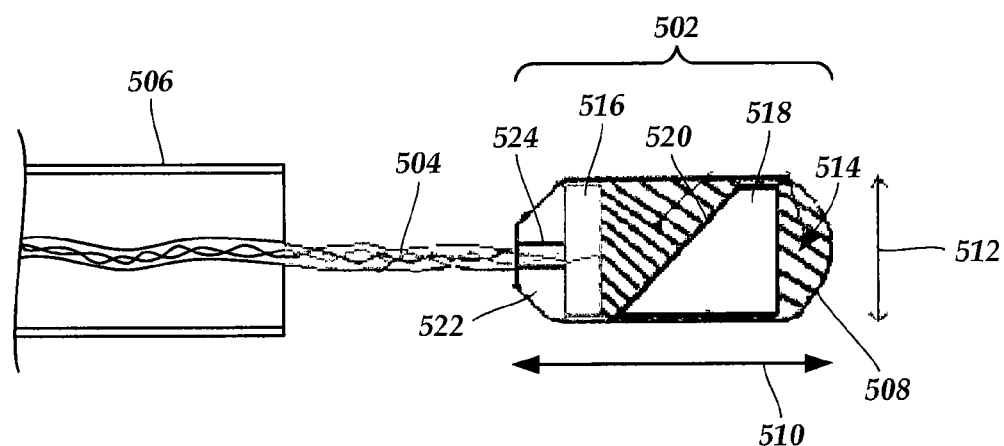
FIG. 5 is a schematic longitudinal cross-sectional view of another embodiment of an imaging core coupled to one or more transducer conductors extending from a lumen of a catheter, according to the invention.

In at least some embodiments, the one or more transducers are disposed entirely proximal to the magnet. FIG. 5 is a schematic longitudinal cross-sectional view of another embodiment of an imaging core 502 coupled to one or more transducer conductors 504 extending from a catheter 506. The imaging core 502 includes a body 508 with a longitudinal length 510 and a diameter 512. The body 508 defines an inner chamber 514 in which one or more fixed transducers 516 and a rotatable magnet 518 are disposed. In at least some embodiments, the magnet 518 has a longitudinal axis that is parallel to the longitudinal length 510 of the imaging core 502. In at least some embodiments, the magnet 518 rotates about the longitudinal axis.

The one or more transducers 516 are electrically coupled to the one or more transducer conductors 504 and the magnet 518 includes a tilted reflective surface 520 configured and arranged to reflect acoustic signals transmitted from the one or more transducers 516 outward from the body 508 toward patient tissue. In at least some embodiments, the one or more transducers 516 are positioned at a proximal end of the imaging core 502 and the magnet 518 is positioned distal to the one or more transducers 516. In at least some embodiments, the one or more transducers 516 are coupled to one or more of a support hub 522, a fixed shaft 524, or the body 508.

In at least some embodiments, the diameter 512 of the imaging core 502 is no greater than 0.8 millimeters. In at least some embodiments, the diameter 512 of the imaging core 502 is no greater than 0.7 millimeters. In at least some embodiments, the diameter 512 of the imaging core 502 is no greater than 0.6 millimeters. In at least some embodiment, the longitudinal length 510 of the imaging core 502 is substantially less than a longitudinal length of the catheter 506.

In at least some embodiments, the body 508 is filled with a sonolucent fluid. In at least some embodiments, the body 508 is filled with a ferrofluid. In at least some embodiments, one or more sonolucent materials are disposed over the reflective surface 520 so that the magnet 518 and sonolucent material(s) have an even weight distribution around the axis of rotation of the magnet 518. In at least some embodiments, the magnet 518 and sonolucent material(s) collectively are substantially cylindrically shaped.

Figure 6:
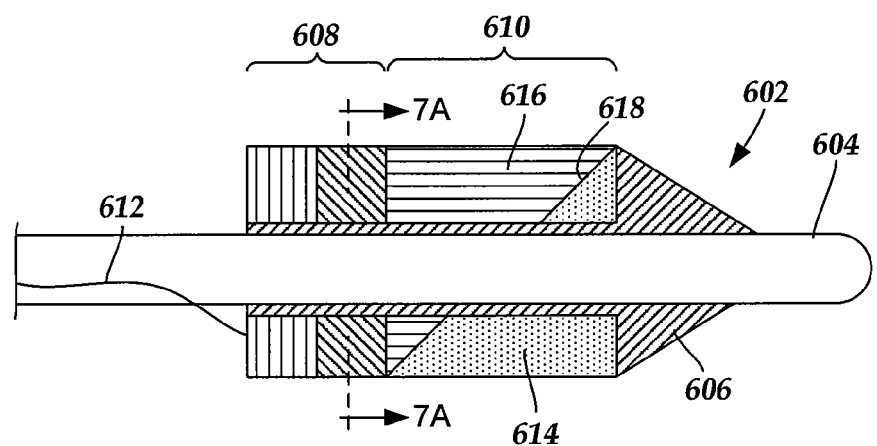
FIG. 6 is a schematic longitudinal cross-sectional view of one embodiment of an imaging core coupled to a guidewire, according to the invention.

In alternate embodiments, the imaging core can be delivered to a target imaging site without using the catheter. In at least some embodiments, the imaging core is configured and arranged to couple to a guidewire insertable into a patient. FIG. 6 is a schematic longitudinal cross-sectional view of one embodiment of an imaging core 602 coupled to a guidewire 604. The imaging core 602 includes a body 606 configured and arranged to receive the guidewire 604. The body 606 can receive the guidewire 604 in many different ways. For example, the body 606 can include a lumen through which the guidewire 604 extends.

The imaging core 602 also includes one or more fixed transducers 608 and a rotatable rotary unit 610. In at least some embodiments, the one or more transducers 608 are ring-shaped. In at least some embodiments, the one or more transducers 608 are C-shaped. In at least some embodiments, the one or more transducers 608 are in electrical communication with the control module (104 in FIG. 1) via one or more transducer conductors 612. In at least some embodiments, at least a portion of the one or more transducer conductors 612 extend along the guidewire 604. The rotary unit 610 includes a magnet 614 and one or more sonolucent materials 616. In at least some embodiments, the rotary unit 610 is substantially cylindrically shaped. In at least some embodiments, the one or more transducers 608 are fixedly coupled to the body 606 In at least some embodiments, the magnet 614 has a longitudinal axis that is parallel to the guidewire 604. In at least some embodiments, the magnet 614 rotates about the longitudinal axis.

The magnet 614 includes a tilted reflective surface 618 configured and arranged to reflect acoustic signals transmitted from the one or more transducers 608. In at least some embodiments, the reflective surface 618 is angled to reflect acoustic signals emitted from the one or more transducers 608 to a direction that is roughly perpendicular to the guidewire 604. In at least some embodiments, the one or more sonolucent materials 616 are formed by a molding process. In at least some embodiments, the one or more sonolucent materials 616 have impedance that matches the impedance of patient tissue or patient fluids at a target imaging site. In at least some embodiments, the one or more sonolucent materials 616 are configured and arranged so that the rotary unit 610 has an even weight distribution around the axis of rotation of the rotary unit 610.

Figures 7A, 7B:
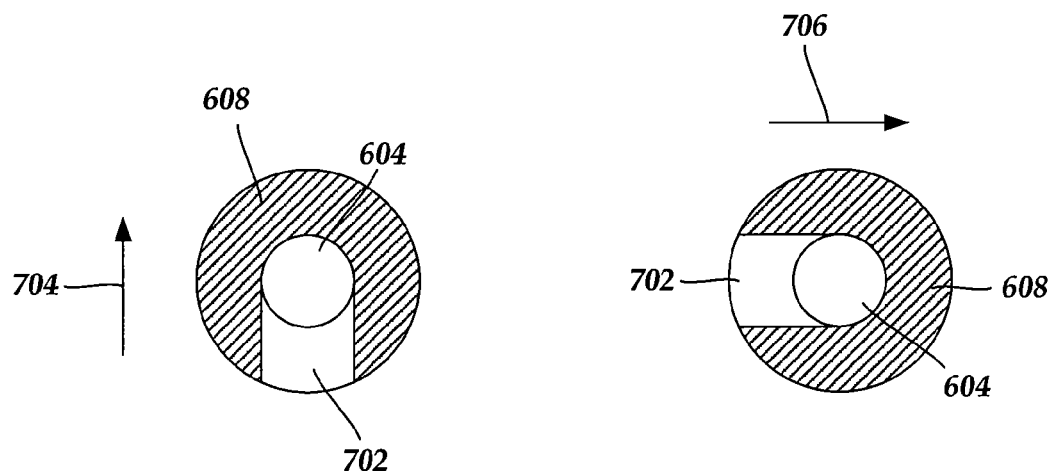
FIG. 7A is a schematic transverse cross-sectional view of one embodiment of the guidewire of FIG. 6 extending through a transducer disposed in the imaging core of FIG. 6 such that a blind spot is formed by the guidewire during imaging when a mirror is tilted to reflect transmitted acoustic energy in a direction indicated by an arrow, according to the invention.
FIG. 7B is a schematic transverse cross-sectional view of one embodiment of the guidewire, transducer, and blind spot of FIG. 7A, the blind spot rotated ninety degrees from the location shown in FIG. 7A due to a ninety degree rotation of a tilted mirror from the first direction shown in FIG. 7A to a second direction indicated by an arrow, according to the invention.

When, as shown in FIG. 6, the one or more transducers 608 are ring-shaped and the guidewire 604 extends through the one or more transducers 608, the guidewire 604 may obstruct some of the acoustic signals from reaching patient tissue, and may also obstruct some of the echo signals from patient tissues from reaching the one or more transducers 608 (i.e., a blind spot may be formed). FIG. 7A is a schematic transverse cross-sectional view of one embodiment of the guidewire 604 extending through the one or more transducers 608. A blind spot 702 is formed over a portion of the one or more transducers 608 because the guidewire 608 obstructs the path of signals transmitting between the one or more transducers 608 and patient tissue. The positioning of the blind spot 702 rotates with the rotation of the magnet (614 in FIG. 6). Arrow 704 shows the direction of the reflected acoustic signals when emitted from the one or more transducers and reflected from the reflective surface (618 in FIG. 6). As shown in FIG. 7A, when the reflected surface is oriented such that acoustic signals emitted from the one or more transducers 608 are reflected upward, the blind spot 702 is positioned beneath the guidewire 608.

Similarly, as shown in FIG. 7B, when the magnet (614 in FIG. 6) is rotated clockwise ninety degrees, the reflective surface (618 in FIG. 6) is also rotated clockwise ninety degrees. Accordingly, arrow 706 shows the direction of reflected acoustic signals being to the right. As a result, the blind spot 702 is rotated clockwise ninety degrees to the left of the guidewire 604.

In at least some embodiments, without the guidewire 604, the imaging core 602 has a diameter that is no greater than 0.5 millimeters. In at least some embodiments, without the guidewire 604, the imaging core 602 has a diameter that is no greater than 0.4 millimeters. In at least some embodiments, without the guidewire 604, the imaging core 602 has a diameter that is no greater than 0.3 millimeters.

In at least some embodiments, with the guidewire 604, the imaging core 602 has a diameter that is no greater than 0.8 millimeters. In at least some embodiments, with the guidewire 604, the imaging core 602 has a diameter that is no greater than 0.7 millimeters. In at least some embodiments, with the guidewire 604, the imaging core 602 has a diameter that is no greater than 0.6 millimeters. In at least some embodiment, the imaging core 602 has a length that is substantially less than a length of the guidewire 604.

Figure 8:
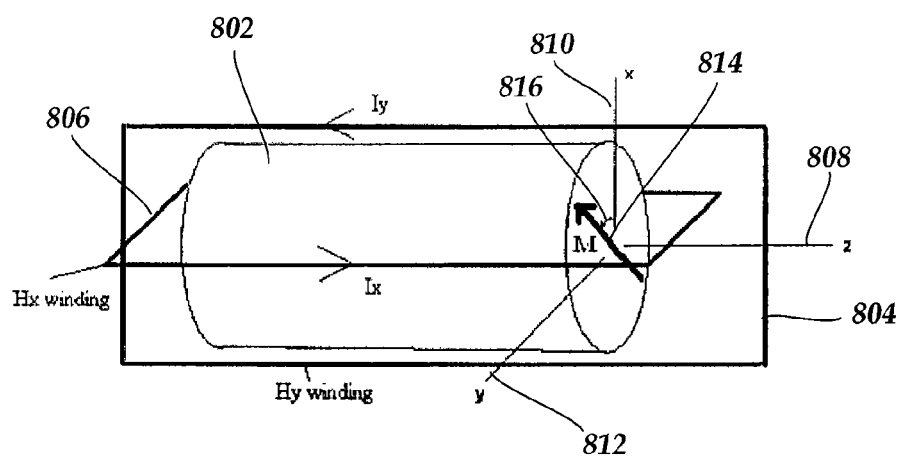
FIG. 8 is a schematic perspective view of one embodiment of a rotating magnet and associated magnetic field windings, according to the invention.

The rotation of the magnets (420, 518, and 614) is driven by windings. FIG. 8 is a schematic perspective view of one embodiment of an exemplary rotatable magnet 802 and associated windings, represented as orthogonal rectangular boxes 804 and 806. Although the windings 804 and 806 are shown as two orthogonal rectangles, it will be understood that the each of the windings 804 and 806 may represent multiple turns of wire. When the windings 804 and 806 are spread out, a band of current may be generated instead of the lines of current shown in FIG. 8. It will also be understood that, as discussed below, there may be more than two orthogonal windings. For example, as discussed below, the magnet 802 may be rotated by three or more orthogonal windings.

The magnet 802 has a longitudinal (z) axis 808 about which the magnet 802 rotates. In order for the magnet 802 to rotate about the longitudinal axis 808, the torque must be about the longitudinal axis 808. Therefore, the magnetic field generated by the windings 804 and 806 must lie in a plane perpendicular to the longitudinal axis 808 with a magnetic field vector H for the windings 804 and 806 rotating about the longitudinal (z)

axis 808 to torque and rotate the magnet 802. FIG. 8 also shows an x-axis 810 and a y-axis 812 that are orthogonal to each other and to the longitudinal axis 808. As shown in FIG. 8, the magnetization vector M 814 of the magnet 802 is in an x-y plane that is perpendicular to the longitudinal axis 848.

The winding 804 produces a magnetic field at the center of the winding 804 that is parallel to the y-axis 812. The winding 806 produces a magnetic field at the center of the winding 806 that is parallel to the x-axis 810. The combined magnetic field vector H for the windings 804 and 806 is given by:

$$H=H_x x'+H_y y'.$$

where x' and y' are unit vectors in the x and y directions, respectively. The magnetization vector M rotates through the angle 816, which is equal to the angular velocity of the magnet 802 times the elapsed time for uniform rotation. Thus, the magnetization vector M is given by:

$$M=M(\cos(\omega t)x'+\sin(\omega t)y').$$

The magnetic moment vector m is given by:

$$m=MV;$$

where M=magnetization vector of the magnet 802 in Tesla; and V=the magnet 802 volume in m³.

The torque τ exerted on the magnet 802 is given by:

$$\tau=m \times H;$$

where τ=the torque vector in N-m; m=the magnetic moment vector in Tesla-m³; H=the magnetic field vector of the windings 804 and 806 in amp/m; and x=the vector cross product.

The vector cross product can be evaluated:

$$\tau=MV(H_y \cos(\omega t) - H_x \sin(\omega t))z'.$$

The vector cross product verifies that the torque produced by the windings 804 and 806 on the magnetic moment vector m is indeed about the longitudinal axis 808. Moreover, the torque will be uniform and independent of time if the magnetic fields generated by the windings 804 and 806 are given by:

$$H_x = -H \sin(\omega t);$$

$$H_y = H \cos(\omega t);$$

thereby yielding a torque τ given by:

$$\tau = MVHz'.$$

The torque is uniform because the magnetic field is uniformly rotating, since $H^2 = H_x^2 + H_y^2$ is independent of time, and the $H_x$ and $H_y$ components describe clockwise rotation of the winding magnetic field vector H about the z' axis. The resulting uniform torque on a symmetric magnet having the magnetization vector M in the x-y plane is an inherent expression of a rotating field electric motor.

Thus, the orthogonal fields produce a magnetic field that uniformly rotates about the longitudinal axis 808 at an angular speed ω. Under operational conditions, the magnetization vector M of the magnet 802 will follow the winding magnetic field vector H of the windings 804 and 806 with a slip angle that is determined by a system drag torque. When the angular speed ω is increased, the drag torque (and the slip angle) increases until the magnet 802 can no longer rotate fast enough to keep up with the magnetic field.

The amount of magnetic torque that may be generated by the motor may be limited by the amount of current that may be passed through the windings 804 and 806 without generating excessive heat in a patient. Heat is generated in the windings 804 and 806 by Joule heating at a rate given by:

$$P = I^2 R;$$

where P=the power dissipated as heat in watts; R=the resistance of the windings 804 and 806; and I=the amplitude of the current in amps.

The value for P is divided by two because sinusoidal current is employed. However the value for P is also multiplied by two because there are two windings 804 and 806. In at least one experiment, it has been estimated that up to 300 mW of heat is readily dissipated in blood or tissue without perceptibly increasing the temperature of the motor. In at least one experiment, it has been estimated that heat dissipation increases to several watts when blood is flowing.

The magnetic field H of the windings 804 and 806 having N turns and inputting current I may be computed. The result follows from the formula for the magnetic field generated by a current-carrying line segment. Typically, the lengths of the long ends of the rectangular-shaped windings 804 and 806 parallel with the longitudinal axis 808 are substantially greater than the lengths of the short ends of the windings 804 and 806. Accordingly, the short ends may not significantly contribute to the magnetic torque. The magnetic field H of the windings 804 and 806 having N turns and inputting current I is given by:

$$H = 2NI/(\pi D \sqrt{1+(D/L)^2}));$$

where N=the number of turns of the windings 804 and 806; D=the winding width in meters; and L=the length of the windings 804 and 806 in meters. NI can be analyzed in terms of the power dissipated in the windings 804 and 806. Although theoretical optimization of all parameters is possible, safety limits may be incorporated into design implementation.

In one exemplary embodiment, rectangular windings 804 and 806 have 8 turns of silver wire with a 2.7 inches (6.86 cm) length, a 0.002 inch (0.005 cm) diameter, and a resistance of 0.5 Ohms. A magnet 802 has a cylindrical shape with an outer diameter of 0.022 inches (0.056 cm), an inner diameter of 0.009 inches (0.022 cm), and a longitudinal length of 0.132 inches (0.34 cm). The magnetization M=1.4 for the magnet 424 having the above-mentioned dimensions formed from neodymium-iron-boron. The maximum power P is equal to 0.3 watts, the maximum current amplitude is 0.77 amps, and the quantity NI is 6.2 amps. Using the above-mentioned values, the torque on the magnet 402 is given by:

$$\tau = 2MV(NI)/(\pi D \sqrt{1+(D/L)^2}))).$$

Inserting the above-mentioned values gives a torque of 4 μN-m=0.4 gm-mm, which is approximately four times larger than an estimated maximum frictional drag on the magnet 802. The corresponding force is about 0.1 gram, or about 30 times the weight of the magnet 802. Although torque may be increased by increasing the magnet radius, it is desirable that the magnet 802 be small enough to be disposed in a wide variety of patient vasculature. Additional considerations for insertion of the catheter into patient vasculature may be considered including, for example, the length of an imaging core (e.g., 408 in FIG. 4, 502 in FIG. 5, or 602 in FIG. 6) (because the relative stiffness of the imaging core may affect maneuverability of the catheter), heat generation, the resistivity of metals at room temperature, and the strength of the materials used to form the magnet 802.

In at least some embodiments, up to six amps of current may be utilized by the motor. Thus, in a preferred embodiment, the components of the imaging core are capable of withstanding up to six amps of current without heating. Low power electronic components are currently available to source six amps of current at low voltage. Additionally, previous studies have shown that flexible stranded leads with an equivalent diameter of approximately 0.015 inches (0.04 cm) can withstand up to six amps of current, while also, being capable of fitting through a catheter with a one-millimeter outer diameter.

From the equation τ=m×H (see above), it can be seen that a given magnet can be rotated with a given torque if an equivalent magnetic field is applied from a three-phase winding. In at least some embodiments, a magnetic field at a centerpoint of a winding in a three-phase winding is given by:

$$H_0 = 3NI_0/(4\pi r);$$

Where $H_0$=the magnetic field at the centerpoint of the winding in amp/m; N=the number of turns of the windings; $I_0$=the amplitude of the winding current in amps; and r=the radius of the windings in meters. Previous experiments have shown that a current of 2 amps is sufficient to produce enough torque to rotate the magnet at 30 Hz when the windings are disposed over the magnet. In one particular embodiment, when N=1; $I_0$=2; and r=approximately 0.002, $H_0$=approximately 290 amp/m. Substituting 290 amp/m into the above equation, increasing r to approximately 6 inches (0.15 m), and solving for N yields windings with approximately 100 turns. Thus, external windings with a radius of 6 inches (0.15 m) and with approximately 100 turns produces a magnetic field of approximately 290 amp/m when 2 amps of current are passed through those external windings.

In at least some embodiments, a magnet (see e.g., 420 in FIG. 4, 518 in FIG. 5, or 614 in FIG. 6) is configured and arranged to operate at a target speed of 30 Hz at 2 amps. In at least some embodiments, the magnet is capable of rotating at more than 110 Hz. In at least some embodiments, the magnet is capable of rotating at more than 100 Hz. In at least some embodiments, the magnet is capable of rotating at more than 90 Hz.

Figure 9:
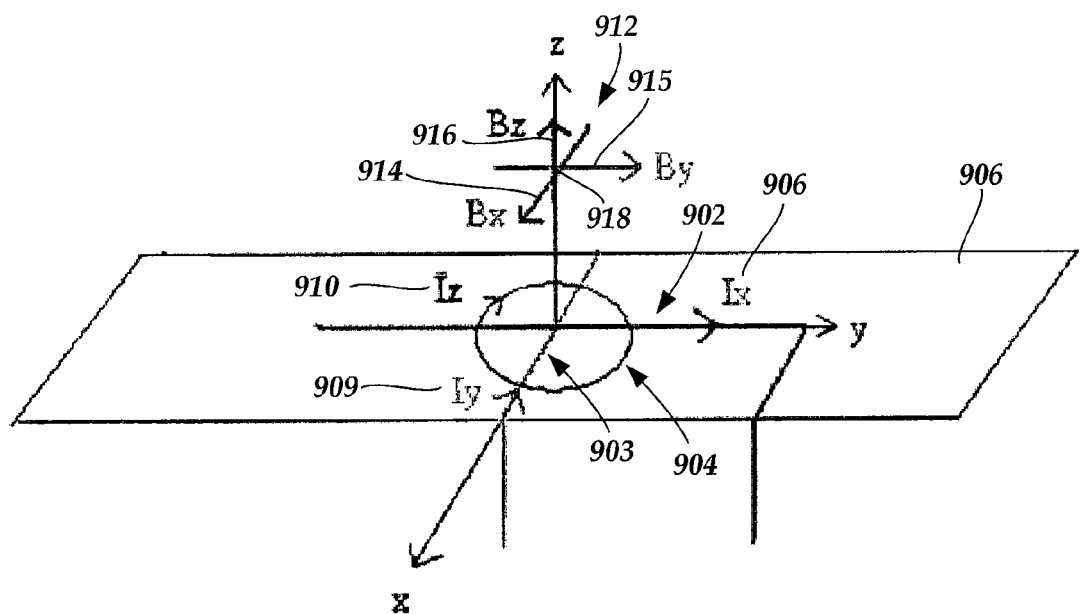
FIG. 9 is a schematic perspective view of one embodiment of portions of three orthogonal magnetic field windings positioned on a plane that form a magnetic field above the plane, according to the invention.

As discussed above, in at least some embodiments the windings are disposed external to the patient into which the magnet is disposed. The extracorporeal windings form a magnetic field within the patient at a target imaging site. FIG. 9 is a schematic perspective view of one embodiment of portions of three orthogonal windings 902-904 positioned on a plane 906. Currents Ix 908, Iy 909, and Iz 910 transmit through the portions of the orthogonal windings 902-904, respectively, as shown by arrows. When currents 908-910 are transmitted through the windings 902-904 in the directions indicated, a magnetic field 912 is formed having three orthogonal components Bx 914, By 915, and Bz 916, respectively, at the intersection 918 of the orthogonal components Bx 914, By 915, and Bz 916. In at least some embodiments, the intersection 918 represents a hypothetical location of a rotatable magnet (see e.g., 420 in FIG. 4, 518 in FIG. 5, or 614 in FIG. 6) within a patient. In at least some embodiments, the portions of the windings 902 and 903 positioned on the plane 906 are straight. In at least some embodiments, the portion of the winding 904 positioned on the plane 906 is a circular loop.

In at least some embodiments, the plane 906 is positioned within a surface suitable for supporting a patient undergoing an imaging procedure. In at least some embodiments, the plane 906 is positioned beneath a surface suitable for supporting a patient undergoing an imaging procedure. In at least some embodiments, the windings 902-904 are configured such that the magnetic field 912 is formed within the patient lying on the surface. In at least some embodiments, the magnetic field 912 has a constant amplitude.

Each of the portions of the orthogonal windings 902-904 positioned on the plane 906 includes a return path (not shown). The return paths of the windings 902-904 may be in any configuration. In preferred embodiments, the return paths are positioned away from the portions of the windings 902-904 positioned on the plane 906. It will be understood that each of the windings 902-904 represents one or more turns of a wire.

When the magnetic field 912 is formed at a height (z) above the plane 906, the magnetic field 912 is given by:

$$H_{x,y} = NI_{x,y}/(2\pi z).$$

In at least some embodiments, z is formed at a location such that the magnetic field is within a patient lying on a surface at, or adjacent to, the plane 906. For example, when a heart of a patient is being imaged, and when the patient is lying on a surface at, or adjacent to, the plane 906, z is no greater than 0.3 meters. In at least some embodiments, N=200 and $I_{x,y}$=3 amps. In at least some embodiments, the windings 902-904 are formed from stranded wire that forms a flexible band of current.

The z-component of the magnetic field 912, Bz 916, is given by;

$$H_z = NI_z/(D[1+(2z/D)^2]^{3/2}).$$

Where D=the diameter of the circular loop. For example, in at least some embodiments, when z=0.3 m; D=0.5 m; and N=200, then a current of 2 amps provides adequate torque to rotate the magnet (see e.g., magnet 802 in FIG. 8).

Figure 10:
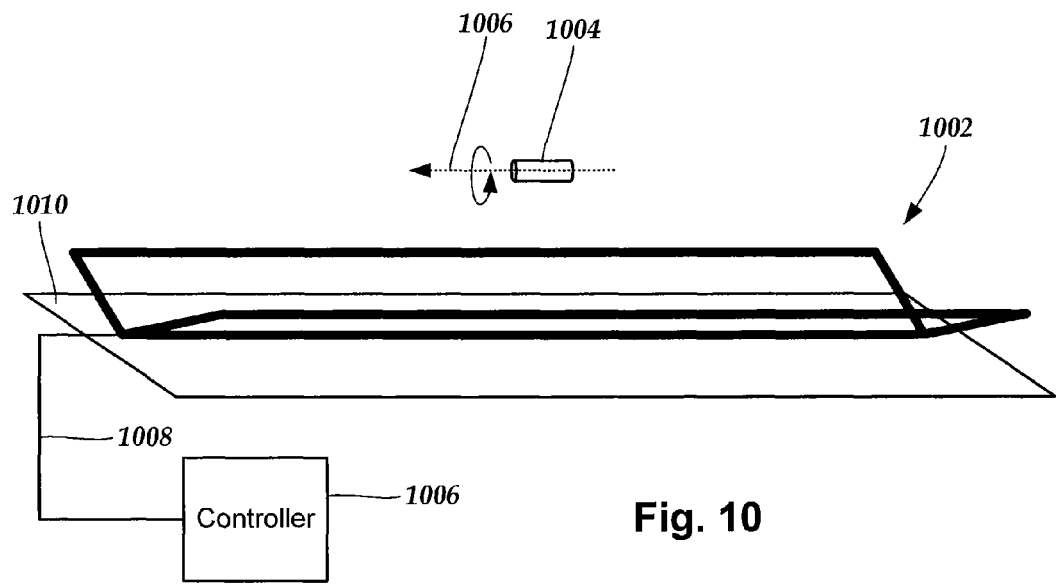
FIG. 10 is a schematic perspective view of one embodiment of a three-phase winding driving a motor magnet, according to the invention.

FIG. 10 is a schematic perspective view of one embodiment of a three-phase winding 1002 generating a magnetic field that drives rotation of a motor magnet 1004 around a longitudinal axis 1006 of the magnet 1004. A controller 1006 is coupled to the three-phase winding 1002 by one or more conductors 1008. In at least some embodiments, the controller 1006 provides power for generating the magnetic field. In FIG. 10, the three-phase winding 1002 is shown disposed on a plane 1010. In at least some embodiments, the plane 1010 is a bed on which a patient may lie during a procedure. In at least some embodiments, the three-phase winding 1002 may be repositioned to allow patient access to the bed. In at least some embodiments, the three-phase winding 1002 may be used by the patient as an arm rest during a procedure.

In at least one previous experiment, a current of no greater than 2 amps has been shown to rotate the motor magnet 1004 at 30 Hz. In at least one previous experiment, a current of no greater than 2 amps has been shown to generate a magnetic field of 290 amps/m. In this experiment, the sides of the windings measured 12 inches (30.5 cm) and each winding contained 100 turns of American Wire Gauge #18 insulated copper magnet wire. It will be understood that in some embodiments, the motor magnet 1004 is significantly smaller in relation to the windings 1008-1010 than is shown in FIG. 10.

Figure 11:
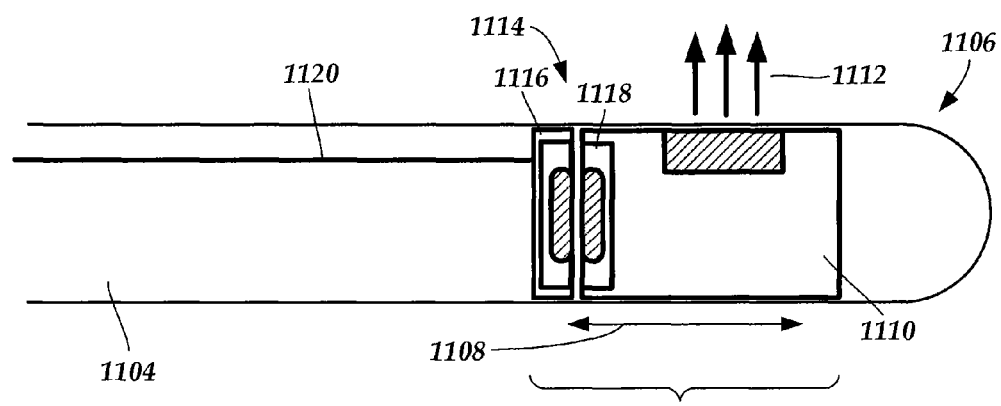
FIG. 11 is a schematic longitudinal cross-sectional view of an alternate embodiment of a distal end of a catheter, the distal end of the catheter including an imaging core disposed in the catheter and having a transformer and one or more rotating transducers, according to the invention.

In alternate embodiments, the imaging core described above can be implemented within a catheter using a transformer and one or more rotating transducers without using a mirror. FIG. 11 shows a longitudinal cross-sectional view of one embodiment of an imaging core 1102 disposed in a distal end of a lumen 1104 of a catheter 1106. The imaging core 1102 has a longitudinal length 1108 and includes one or more rotatable transducers 1110. In at least some embodiments, rotation of the one or more transducers 1110 is driven by an applied magnetic field external to the catheter 1102. In at least some embodiments, the one or more transducers 1110 are positioned such that the acoustic signals output from the one or more transducers 1110 are directed at angles that are not parallel with to the longitudinal axis of the imaging core 1102, as shown by arrows 1112. In at least some embodiments, a transformer 1114 with a stationary component 1116 and a rotating component 1118 is coupled to the one or more transducers 1110 and is used to transmit electrical signals to and from the one or more transducers 1110 via one or more transducer conductors 1120 extending from the stationary component 1116 to the control module (104 in FIG. 1). In at least some embodiments, a magnet is coupled to, or disposed on, at least one of the rotating component 1118 or the one or more transducers 1110. The magnet is configured and arranged to rotate the rotating component 1118 and the one or more transducers 1110 via an applied magnetic field external to the catheter 1102.

As discussed above, the direction of the vector is in a plane perpendicular to the longitudinal axis of the magnet (see e.g., 420 in FIG. 4, 518 in FIG. 5, or 614 in FIG. 6). In at least some embodiments, the direction of the vector of the magnetic field 902 is adjustable so that the direction of the vector can adjust as the magnet changes orientation. When the magnet is disposed in a patient, at least one of the location or orientation of the magnet may not be detectable via the naked eye. In at least some embodiments, at least one of the location or orientation of the magnet is determined by one or more imaging methods, such as fluoroscopy. In at least some embodiments, one or more sensors (e.g., magnetic sensors, or the like) are disposed in proximity to the magnet that can be used to determine one or more of the location or orientation of the magnet. In at least some embodiments, one or more extracorporeal sensors (e.g., magnetic sensors, or the like) can be used to determine one or more of the location or orientation of the magnet.

In at least some embodiments, a combination of two or more of the abovementioned techniques can be used to determine one or more of the location or orientation of the magnet. For example, in at least some embodiments one or more sensors may be positioned in proximity to the magnet and implantable into the patient, while a plurality of sensors remain external to the patient. The implantable sensor may identify the angular orientation of the magnet, and this data may be used to accept only data from the external sensors that have the proper frequency and proper phase angle of the magnet while rejecting data obtained from external sensors with an improper frequency and phase angle, thereby further increasing the signal-to-noise ratio in the external sensor data.

In at least some embodiments, when one or more external sensors are used, the external sensors may include two triaxial magnetic sensors, including six individual sensors, that measures the x, y, and z components of a rotating magnetic field of the magnet at two locations external to the patient. In at least some embodiments, magnetic field sensing of the rotating magnet is facilitated by sensing only magnetic fields that rotate in phase with the magnet winding drive currents. Data from the external sensors may be inverted to find the x, y, and z coordinates of the rotating magnet (and IVUS transducer), and the spatial orientation of the magnet. This data can be used to form a three dimensional image of surrounding tissue (e.g., bends in an artery) during pull back imaging.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An imaging assembly for an intravascular ultrasound system, the imaging assembly comprising:
    a catheter having a longitudinal length, a distal end, and a proximal end, the catheter defining a lumen extending along the longitudinal length of the catheter from the proximal end to the distal end, the catheter configured and arranged for insertion into the vasculature of a patient;
    an imaging core with a longitudinal length that is substantially less than the longitudinal length of the catheter, the imaging core configured and arranged for being disposed in the lumen and also for extending out from the distal end of the catheter, the imaging core comprising
        a body having a proximal end and a distal end and defining at least one inner chamber,
        a tubular shaft oriented within the body,
        a rotatable magnet disposed in the body, wherein the magnet is configured and arranged to be driven to rotate by a magnetic field generated external to the catheter,
        a tilted reflective surface configured and arranged to rotate with the magnet, and
        at least one fixed transducer disposed in the body and supported by the tubular shaft, the at least one transducer configured and arranged for transforming applied electrical signals to acoustic signals and also for transforming received echo signals to electrical signals; and
    at least one transducer conductor electrically coupled to the at least one transducer, a portion of the at least one transducer conductor oriented within the tubular shaft, the at least one transducer conductor configured and arranged to extend out from the body and into the lumen of the catheter when the imaging core is extended from the catheter;
    wherein the imaging core is attached to the imaging assembly only by a tether that extends proximally from the imaging core, the tether comprising said at least one transducer conductor.

2. The imaging assembly of claim 1, further comprising at least two magnetic field windings disposed external to the catheter and configured and arranged to provide the magnetic field.

3. The imaging assembly of claim 1, wherein the tubular shaft couples the at least one transducer to the proximal end of the body.

4. The imaging assembly of claim 3, wherein the magnet defines an aperture extending along at least a portion of its length, a portion of the rotatable magnet surrounds the tubular shaft, the tubular shaft oriented in the aperture of the magnet.

5. The imaging assembly of claim 1, wherein a ferrofluid is disposed in the body such that the magnet is surrounded by the ferrofluid.

6. The imaging assembly of claim 1, wherein the at least one sonolucent material is disposed over the tilted reflective surface.

7. The imaging assembly of claim 1, wherein at least a portion of the magnet is positioned proximal to the at least one transducer.

8. The imaging assembly of claim 1, wherein the imaging core further comprises a support hub disposed in the body proximal to the at least one transducer, the support hub providing structural support to the imaging core proximal to the at least one transducer.

9. The imaging assembly of claim 1, wherein the tilted reflective surface is tilted at an angle such that when an acoustic beam is transmitted from the at least one transducer to the reflective surface, the acoustic beam is reflected in a direction that is not parallel the longitudinal axis of the magnet.

10. The imaging assembly of claim 1, wherein the tilted reflective surface is positioned distal to the at least one transducer.

11. The imaging assembly of claim 1, wherein said imaging core body comprises a proximal portion having a taper, said taper increasing in size as the proximal portion is traversed in a distal direction.

12. The imaging assembly of claim 1, wherein the imaging core further comprises a sensing device, the sensing device configured and arranged for sensing the angular position of the magnet.

13. The imaging assembly of claim 1, wherein the imaging core has a transverse outer diameter that is not greater than 0.8 millimeters.

14. An intravascular ultrasound imaging system comprising:
   the imaging assembly of claim 1; and
   a control module coupled to the imaging core, the control module comprising
      a pulse generator configured and arranged for providing electric signals to the at least one transducer, the pulse generator electrically coupled to the at least one transducer via the at least one transducer conductor, and
      a processor configured and arranged for processing received electrical signals from the at least one transducer to form at least one image, the processor electrically coupled to the at least one transducer via the at least one transducer conductor.

15. A method for imaging a patient using an intravascular ultrasound imaging system, the method comprising:
   providing the imaging assembly recited in claim 1;
   inserting the catheter into patient vasculature;
   extending the imaging core out from a distal end of the catheter so that the imaging core remains coupled to the control module via the tether;
   transmitting at least one electrical signal from the control module to the at least one transducer;
   generating a magnetic field to cause the magnet to rotate;
   transmitting at least one acoustic signal from the at least one transducer to patient tissue via reflection from the reflective surface of the magnet;
   receiving at least one echo signal from a tissue-boundary between adjacent imaged patient tissue by the imaging core; and
   transmitting at least one transformed echo signal from the at least one transducer to the control module for processing.

16. The method of claim 15, wherein transmitting at least one electrical signal to the at least two magnetic field windings comprises transmitting the at least one electrical signal from the control module.

* * * * *